(12) United States Patent
Suehira (10) Patent No.: US 8,760,664 B2
(45) Date of Patent: Jun. 24, 2014

(54) IMAGING APPARATUS AND IMAGING METHOD USING OPTICAL COHERENCE TOMOGRAPHY

(75) Inventor: Nobuhito Suehira, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 172 days.

(21) Appl. No.: 12/991,734

(22) PCT Filed: Jul. 6, 2009

(86) PCT No.: PCT/JP2009/062642
§ 371 (c)(1),
(2), (4) Date: Nov. 9, 2010

(87) PCT Pub. No.: WO2010/005091
PCT Pub. Date: Jan. 14, 2010

(65) Prior Publication Data
US 2011/0058175 A1 Mar. 10, 2011

(30) Foreign Application Priority Data

Jul. 7, 2008 (JP) .................................. 2008-177158
Jun. 25, 2009 (JP) .................................. 2009-151483

(51) Int. Cl.
*G01B 11/02* (2006.01)
*G01B 9/02* (2006.01)

(52) U.S. Cl.
USPC ............ 356/497; 356/455; 356/456; 356/450

(58) Field of Classification Search
USPC .................. 356/450–452, 454–456, 497, 504
See application file for complete search history.

(56) References Cited

U.S. PATENT DOCUMENTS 4,989,971 A * 2/1991 McDonald .................... 356/73.1
5,018,855 A   5/1991 Davison et al.
(Continued)

FOREIGN PATENT DOCUMENTS

| JP | 11-325849 A | 11/1999 |
| JP | 2006-122649 A | 5/2006 |
| JP | 2007-007297 A | 1/2007 |

OTHER PUBLICATIONS

International Search Report and Written Opinion of the International Searching Authority mailed Oct. 19, 2009 in International Patent Application No. PCT/JP2009/062642.

(Continued)

*Primary Examiner* — Gregory J Toatley
*Assistant Examiner* — Hina F Ayub
(74) *Attorney, Agent, or Firm* — Fitzpatrick, Cella, Harper & Scinto (57) ABSTRACT

Provided is an imaging apparatus using Fourier-domain optical coherence tomography, the imaging apparatus removing noises caused by the autocorrelation component of returning light to obtain a high-resolution tomographic image. A first switching unit 17 switches a first state in which returning light 12 is combined with reference light (a state in which the returning light 12 is conducted to a combining unit 22) and a second state different from the first state (a state in which the light path of the returning light 12 is blocked or changed). A controlling unit 18 controls the switching unit 17 to change the first and the second state. A interferometric information acquiring unit 19 acquires interferometric information on the returning light 12 and the reference light 14 using the reference light 14 or the returning light 12 detected by the detecting unit 16 in the second state and the combined light 15.

14 Claims, 8 Drawing Sheets

(56) References Cited

U.S. PATENT DOCUMENTS

| | | | |
|---|---|---|---|
| 6,243,511 B1* | 6/2001 | Laughlin | 385/18 |
| 6,377,349 B1 | 4/2002 | Fercher | |
| 6,785,634 B2 | 8/2004 | Bachrach et al. | |
| 7,804,599 B2 | 9/2010 | Calderoni | |
| 8,180,131 B2* | 5/2012 | Toth et al. | 382/131 |
| 2002/0167656 A1 | 11/2002 | van den Engh | |
| 2002/0176085 A1* | 11/2002 | Hill | 356/452 |
| 2003/0007155 A1* | 1/2003 | Ota | 356/451 |
| 2004/0075056 A1 | 4/2004 | Bell et al. | |
| 2006/0087616 A1 | 4/2006 | Hanebuchi | |
| 2006/0089548 A1* | 4/2006 | Hogan | 600/316 |
| 2007/0076210 A1* | 4/2007 | Kiesel et al. | 356/454 |
| 2007/0177154 A1* | 8/2007 | Rembe | 356/498 |
| 2007/0177161 A1* | 8/2007 | Ishii et al. | 356/614 |
| 2008/0002183 A1* | 1/2008 | Yatagai et al. | 356/73 |
| 2009/0284749 A1* | 11/2009 | Johnson et al. | 356/497 |
| 2010/0226553 A1 | 9/2010 | Suehira | |
| 2010/0226554 A1 | 9/2010 | Suehira | |
| 2011/0096333 A1 | 4/2011 | Suehira et al. | |
| 2011/0098560 A1 | 4/2011 | Suehira et al. | |
| 2012/0127476 A1* | 5/2012 | de Boer et al. | 356/497 |

OTHER PUBLICATIONS

A.F. Fercher et al., Measurement of intraocular distances by backscattering spectral interferometry, Optics Communications 117 (1995) 43-48, May 15, 1995.

J. Al et al., Synchronous self-elimination of autocorrelation interference in Fourier-domain optical coherence tomography, Optics Letters, vol. 30, No. 21, 2939-2941, Nov. 1, 2005.

J. Al et al., Spectral-domain optical coherence tomography: Removal of autocorrelation using an optical switch, Applied Physics Letters, vol. 88, No. 11, 111115, Mar. 15, 2006.

Office Action dated Dec. 8, 2011, in Russian Application No. 2011104091/(005691).

Notification Concerning Transmittal of International Preliminary Report on Patentability dated Jan. 20, 2011, forwarding International Preliminary Report on Patentability dated Jan. 11, 2011, in counterpart International Application No. PCT/JP2009/062642.

Apr. 16, 2012 Korean Official Action in Korean Patent Appln. No. 10-2011-7001933.

* cited by examiner

IMAGING APPARATUS AND IMAGING METHOD USING OPTICAL COHERENCE TOMOGRAPHY

TECHNICAL FIELD

The present invention relates to an imaging apparatus and an imaging method using optical coherence tomography, specifically to an imaging apparatus and an imaging method used for observing the eye and the skin using the optical coherence tomography.

BACKGROUND ART

There has been put into practical use an imaging apparatus using optical coherence tomography (OCT) taking advantage of coherence of low coherence light (hereinafter referred to as OCT apparatus). The imaging apparatus can obtain a tomographic image with resolution on the order of a wavelength of light incident on an object, which enables providing a high-resolution tomographic image of an object to be detected.

Light from a light source is split into measuring light and reference light by a splitting light path such as a beam splitter. An object to be detected such as the eyes is first irradiated with the measuring light through a measuring light path. The light returning from the object to be detected is then conducted to a detecting position through a detecting light path. The term "returning light" refers to reflected light and scattered light including information on an interface in the direction in which the object to be detected is irradiated with light. The reference light is reflected by a reference mirror through a reference light path to conduct the reflected light to the detecting position. The detection and analysis of the coherent light of the returning light and the reference light with a detector provides a tomographic image of the object to be detected.

Japanese Patent Application Laid-Open No. H11-325849 discloses an OCT configuration in which the position of a reference mirror is discontinuously changed three times in measuring one point of an object to be detected to obtain wavelength spectra and then the calculation of the spectra provides a tomographic image.

Furthermore, there is disclosed a Fourier-Domain OCT apparatus (hereinafter referred to as PD-OCT apparatus) in which wavelength spectra are obtained with a reference mirror of the OCT apparatus fixed and a tomogram is measured by Fourier transformation, in a paper; A. F. Fercher, C. K. Hitzenberger, G. Kamp, S. Y. El-Zaiat, Opt. Commun. 117, 43-48, (1995). The FD-OCT apparatus includes a system using a spectroscope (SD-OCT: Spectral Domain OCT) and a system sweeping the wavelength of a light source (SS-OCT: Source Swept-OCT).

DISCLOSURE OF THE INVENTION

It requires more time for the OCT apparatus disclosed in Japanese Patent Application Laid-Open No. H11-325849 to perform measurement than for the FD-OCT apparatus capable of obtaining tomographic images collectively in the depth direction, because the OCT apparatus moves the reference mirror.

On the other hand, the FD-OCT apparatus can use the fixed reference mirror in collectively obtaining tomographic images in the depth direction. However, the autocorrelation components of the reference light and the returning light are included in the combined light of the reference light and the returning light as noise. For avoiding this, the reference mirror located in an optically equivalent position may be away from the object to be detected to be isolated from these components. Also for avoiding this, coherence gate may be away from the object to be detected in order to be isolated from those components.

However, the reference mirror located in an optically equivalent position being away from the object sometimes decreases measuring sensitivity (sensitivity of the sensor), and the autocorrelation components of the reference light and the returning light need to be removed from the combined light to perform high accuracy measurement. In particular, the autocorrelation component of the returning light is varied with locations to be measured, so that the autocorrelation component of the returning light needs to be sequentially obtained to be removed from the combined light.

The present invention has been made in view of the above problems and it is an object of the present invention to provide an optical tomographic imaging apparatus configured in the following manner and a method of imaging an optical tomographic image.

According to the present invention, an optical tomographic imaging apparatus is provided which splits light from a light source into measuring light and reference light, conducts the measuring light to an object to be detected through a measuring light path and conducts the reference light to a reference mirror through a reference light path and images a tomographic image of the object to be detected using returning light based on the measuring light reflected or scattered by the object to be detected, the reference light reflected by the reference mirror and combined light based on the returning light and the reference light including: units for controlling the transmittance of light arranged in each of the measuring light path and the reference light path; a controlling unit for controlling time interval of change in the transmittance of light in the units for controlling the transmittance of light based on a set profile; a unit for obtaining wavelength spectra data of each of the returning light, reference light and combined light which is based on light from the light source and obtained by the control of the time interval based on the profile; and a calculating unit in which wavelength spectra data of the obtained returning light, reference light and combined light is used to calculate at least any of the optical components.

A method of imaging an optical tomographic image according to the present invention includes the steps of: splitting light from a light source into measuring light and reference light, conducting the measuring light to an object to be detected and conducting the reference light to a reference mirror; and imaging a tomographic image of the object to be detected using returning light based on the measuring light reflected or scattered by the object to be detected, the reference light reflected by the reference mirror and combined light based on the returning light and the reference light; and in that units for controlling the transmittance of light arranged in each of a measuring light path for conducing the measuring light and a reference light path for conducting the reference light are controlled based on a profile in which a time interval is set to obtain the returning light, the reference light and the combined light based on the light from the light source, and wavelength spectra data acquired from each of the obtained returning light, reference light and combined light is used to calculate at least any of the optical components.

Another imaging apparatus using Fourier-domain optical coherence tomography includes:
 a light source for emitting light;
 a splitting unit for splitting light from the light source into reference light and measuring light;

a detecting unit for detecting combined light into which the returning light obtained by radiating the measuring light to an object to be detected and the reference light are combined;

one of a first switching unit for switching between a first state in which the detecting unit can detect the combined light and a second state in which the detecting unit can detect the reference light, and a second switching unit for switching between the first state and a third state in which the detecting unit can detect the measuring light;

a controlling unit for controlling one of the first switching unit to switch between the first state and the second state, and the second switching unit to switch between the first state and the third state; and a interferometric information acquiring unit for acquiring interferometric information on the returning light and the reference light by using the combined light detected by the detecting unit in the first state and one of the reference light detected in the second state and the measuring light detected in the third state.

Another imaging method using a Fourier domain optical coherence tomography includes:

generating a light;

splitting the light into a reference light and a measuring light;

irradiating the measuring light to an object to be detected;

detecting the combined light obtained by combining the reference light and the returning light obtained by the irradiation;

switching between a first state in which the combined light can be detected and a second state in which the reference light can be detected, or between the first state and a third state in which the measuring light can be detected; and obtaining interferometric information on the returning light and the reference light by using the combined light detected in the first state and one of the reference light detected in the second state and the measuring light detected in the third state.

According to the present invention, the removal of the autocorrelation component of the reference light allows providing a high accuracy tomographic image.

Further features of the present invention will become apparent from the following description of exemplary embodiments with reference to the attached drawings.

BEST MODES FOR CARRYING OUT THE INVENTION

First Embodiment

Figure 1A:
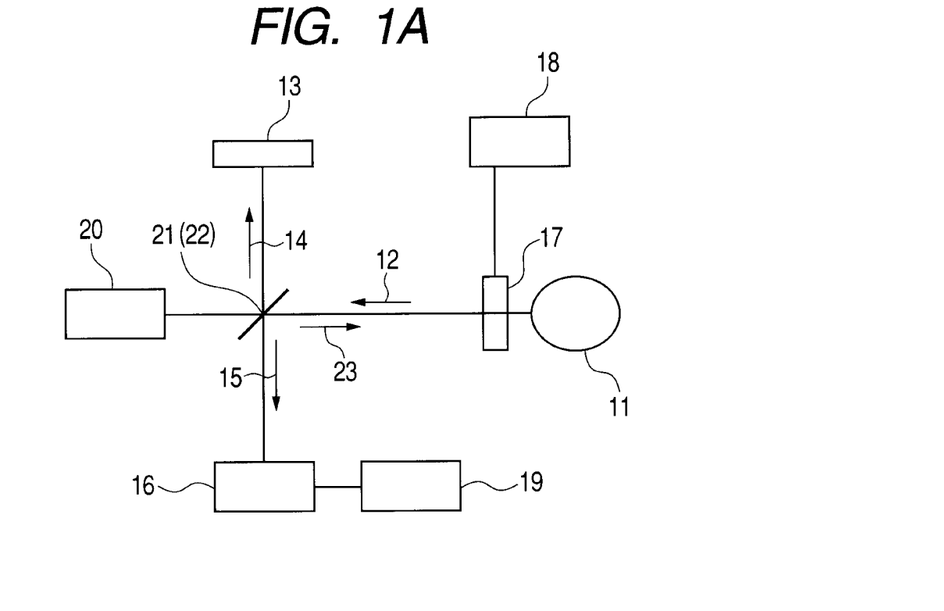
FIGS. 1A and 1B are schematic diagrams for describing imaging apparatus using optical coherence tomography according to the present embodiment.
Figure 1B:
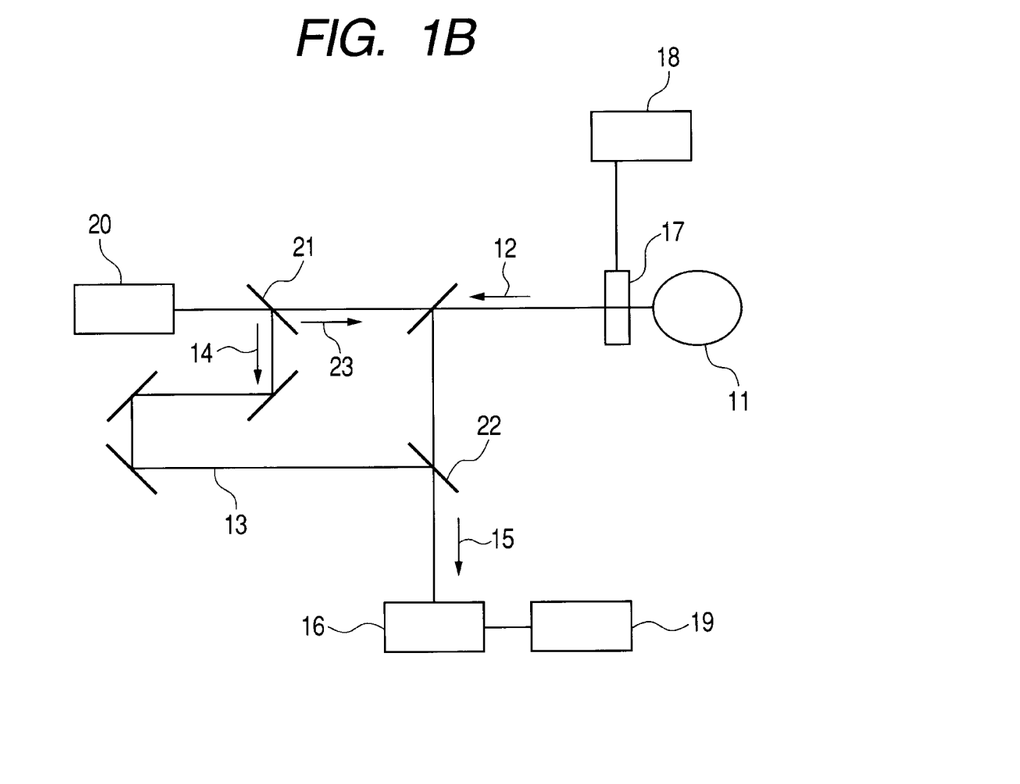

An imaging apparatus using a Fourier domain optical coherence tomography according to the present embodiment is described below with reference to FIGS. 1A and 1B. FIG. 1A illustrates a Michelson type interferometer and FIG. 1B illustrates a Mach-Zehnder type interferometer. In FIG. 1A, a splitting unit 21 and a combining unit 22 is configured of common members. In FIG. 1B, on the other hand, the splitting unit 21 and the combining unit 22 are configured of different members.

The present invention is not limited to the apparatus presented by either of FIGS. 1A and 1B in which switching unit 17 (also referred as the first switching unit) such as a shutter is located on the measuring light path. The switching unit (also referred as the second switching unit) such as shutter may also be located on the reference light path. The apparatus may include only one of the first switching unit and the second switching unit, and the apparatus may include both of them.

The FD-OCT (Fourier Domain OCT) includes two types, namely SD-OCT (Spectral Domain OCT) and SS-OCT (Source Swept-OCT). Although in this embodiment, the following explanation is accompanied with SD-OCT type, the invention may also include the apparatus using SS-OCT.

(Imaging Apparatus)

A light source 20 generates light (low coherence light). A super luminescent diode (SLD) can be applied to the light source 20. An amplified spontaneous emission (ASE) can also be applied to the light source 20. In addition, ultrashort pulse laser such as titanium sapphire laser can also be applied to the light source 20. Any others that can generate low coherence light may be applied to the light source 20. The wavelength of light generated from the light source 20 is 400 nm to 2 μm, which is not limited in particular. The resolution to the depth direction increases as the bandwidth of the wavelength becomes wide. Generally, when the central wavelength is 850 nm, the resolution is 6 μm within the wavelength of 50 nm and the resolution is 3 μm within the wavelength of 100 nm.

A splitting unit 21 splits light from the light source 20 into reference light 14 and measuring light 23. A beam splitter or a fiber coupler can be applied to the splitting unit 21. Any others that can split light may be applied to the splitting unit 21. A ratio of the splitting may also be selected as proper to the object to be detected.

A detecting unit (spectroscope) 16 detects combined light 15 of returning light 12 obtained by radiating the measuring light 23 to the object to be detected 11 (including living body parts such as eye of fundus) and the reference light 14 (reflected by a reference unit 13 such as mirrors to be set on the reference light path. The measuring light 23 may be radiated to the object to be detected 11 by an optical unit such as a lens located on the measuring light path. The detecting unit 16 has a spectroscopic device for dispersing the combined light 15 (for example, a prism 109 in FIG. 2A). The spectroscopic device is a diffraction grating or a prism, and any others that can disperse light may be used. The detecting unit 16 has a sensor (for example, an imaging device 110 in FIG. 2A) for detecting the light dispersed by the spectroscopic device. The sensor is a line sensor or a two dimensional sensor, and any others that can detect light may be used.

A switching unit 17 switches between a first state in which the detecting unit 16 can detect the combined light 15 (a state in which the returning light 12 is guided to the combining unit 22) and a second state in which the detecting unit can detect the reference light 14. The switching unit 17 is also referred as a first switching unit in which the first switching unit is located on the measuring light path. A switching unit of this embodiment may be located on the reference light path as described above, which is referred as a second switching unit. The first switching unit and the second switching unit may be located on the same apparatus. The second switching unit can switch between the first state and a third state in which the detecting unit 16 can detect the measuring light.

The switching unit 17 is desirably configured such that the light path of the measuring light 23 or the returning light 12 can be blocked. At this point, the second state is in a blocked state. The switching unit 17 is desirably configured such that the transmittance of the measuring light 23 or the returning light 12 can be controlled. In those cases, a shutter (described later) can be applied to the switching unit 17, but any others that can block the light path may be applied.

The switching unit 17 may be configured such that the light path of the measuring light 23 or the returning light 12 can be changed. At this point, the second state is in the changed state. In this case, an optical scanning unit (for example, an XY scanner 104 in FIG. 2A) for scanning the measuring light 23 on the object to be detected 11, for example, can be applied to the switching unit 17, but any others that can change the light path may be applied.

A controlling unit 18 (the first switching unit) controls the switching unit 17 to change the first state and the second state. The controlling unit 18 can control the switching unit (the second switching unit) to switch between the first state and the third state. The controlling unit 18 may control both of the first switching unit and the second switching unit to switch the first state, the second state and the third state. The controlling unit 18 may include two controlling devices to control both of the first switching unit and the second switching unit, and may be configured on a single device to control the first switching unit and the second switching unit. Desirably, the controlling unit 18 controls the switching unit 17 based on a predetermined timing (for example, FIGS. 3A to 3E). At this point, the combined light 15 is detected by the detecting unit 16 at the timing of the first state.

An interferometric information acquiring unit 19 acquires interferometric information (coherence components, an equation 8 described later) on the returning light 12 and the reference light 14 using the reference light 14 detected by the detecting unit 16 in the second state and the combined light 15. It is desirable that the autocorrelation component (an equation 1 described later) of the reference light 14 and the autocorrelation component (an equation 2 described later) of the returning light 12 are subtracted from the combined light 15 (an equation 7 described later) detected by the detecting unit 16. Desirably, the subtraction result (an equation 8 described later) is standardized by the autocorrelation component of the reference light 14. The Fourier transformation of the standardization result (an equation 9 described later) provides the tomographic image of the object to be detected 11.

This allows sequentially providing the returning light 12 which may vary with locations to be measured. Thereby, the autocorrelation component of the returning light 12 can be removed from the combined light 15.

The autocorrelation component is a component by the reference light itself or by the returning light itself, which is included in addition to the coherence component of reference light and the returning light. The combined light of the reference light and the returning light include the autocorrelation component in addition to their coherence component. In order to detect the coherent component, the autocorrelation component of the reference light, which is a component having relatively large amount of light quantity compared to the coherence component, is desirably subtracted from the combined light.

The OCT apparatus desirably includes a light quantity detecting unit (for example, a detector 803 in FIG. 7) for detecting the quantity of the measuring light and a comparing unit (not shown) for comparing the detected light quantity with a predetermined value. When the detected light quantity is different from the predetermined value (predetermined light quantity) or the detected light quantity is out of the range of the predetermined light quantity, the switching unit 17 desirably switches the first state to the second state. As a result, when the light quantity of the measuring light is different from the predetermined light quantity (or is out of the range of the predetermined light quantity), the measuring light is not radiated out of the imaging apparatus (described later in an embodiment 3).

(Imaging Method)

An imaging method using a Fourier domain optical coherence tomography according to the present embodiment at least includes the steps described below.

a) a step of generating a light.

b) a step of splitting the light into a reference light and a measuring light.

c) a step of irradiating the measuring light to an object to be detected.

d) a step of detecting the combined light obtained by combining the reference light and the returning light obtained by the irradiation.

e) a step of switching between a first state in which the detecting unit 16 can detect the combined light and a second state in which the detecting unit can detect the reference light, or between the first state and a third state in which the detecting unit 16 can detect the measuring light.

f) a step of obtaining interferometric information on the returning light and the reference light by using the combined light detected in the first state and one of the reference light detected in the second state and the measuring light detected in the third state.

By using this method, the autocorrelation component of the reference light or the returning light is removed from the combined light, thereby enabling an obtaining of high accuracy interferometric information.

In the step e), the changing may be among the first state, the second state and the third state.

In order to obtain still more accurate tomographic information, the method desirably includes the following steps:

g) a step of subtracting the autocorrelation component of the reference light and the autocorrelation component of the returning light from the combined light.

h) a step of standardizing the subtracted value by the autocorrelation component of the reference light.

i) a step of Fourier transforming the standardized result.

j) a step of obtaining the tomographic image of the object to be detected.

The above steps g) to j) are desirably executed by a subtracting unit, a standardizing unit, a transforming unit, and a tomographic image acquiring unit, respectively. Each of the above units is not necessarily divided into different processors such as CPUs, but a single processor may include each of them.

When the method includes further steps below, the measuring light may not be radiated out of the imaging apparatus when the light quantity of the measuring light is different from the predetermined light quantity (or out of the range of the predetermined light quantity):

k) a step of detecting the light quantity of the measuring light.

l) a step to change to the second state when the light quantity is different from the predetermined light quantity.

Second Embodiment

An optical tomographic imaging apparatus according to another embodiment is described below with reference to FIG. 2A. Light from a light source 101 through a splitting light path is split into measuring light 112 and reference light 114. The measuring light 112 is conducted to the object 106 to be detected through a measuring light path and a returning light 113 of the measuring light reflected or scattered by the object to be detected 106 is conducted to a detection position through a detecting light path. On the other hand, the reference light 114 is conducted to a reference mirror 115 through a reference light path and the reference light reflected by the reference mirror 115 is conducted to the detection position. The use of combined light of the returning light 113 and the reference light 114 which are conducted to the detection position images the tomographic image of the object to be detected. At this point, units 117-1 and 117-2 for controlling the transmittance of light are arranged on the reference light path and the measuring light path respectively. The unit for controlling the transmittance of light is configured to control time interval of change in the transmittance of light based on the profile set by a control unit 111. A unit for acquiring wavelength spectrum data 108 is configured to acquire the wavelength spectrum data of the returning light 113, the reference light 114 and the combined light based on the light from the light source that are acquired by controlling time interval based on the profile. A calculating unit 111 is configured to use the wavelength spectrum data of the acquired returning light, the reference light and the combined light to calculate at least any of those optical components.

The units 117-1 and 117-2 for controlling the transmittance of light may be configured with an optical switching device for switching the transmittance and cutoff of light. In addition, the optical switching device may be configured with either of a mechanical or an electrical shutter. The mechanical or the electrical shutter may be configured to enable the transmittance of light to be controlled. The control unit 111 may be configured to enable control based on the profile in which the acquiring time for the returning light is set longer than the acquiring time for the reference light. Furthermore, the control unit 111 may be adapted to include an optical amplifier (for example, an optical amplifier 517 in FIG. 2B) for amplifying the returning light.

A method of imaging an optical tomographic image according to the present embodiment can be configured as follows. The foregoing units 117-1 and 117-2 for controlling the transmittance of light are controlled based on the profile with the set time interval to obtain the returning light 113, the reference light 114 and the combined light which are based on the light from the light source. The wavelength spectrum data obtained from the acquired returning light, the reference light and the combined light is used to calculate at least any of those optical components.

In calculating the optical component, the wavelength spectrum data obtained from the acquired returning light, the reference light and the combined light is used to enable the subtraction of the autocorrelation components of the reference light and the returning light from the component of the combined light. Furthermore, in calculating a component of the light, the above subtraction result may be configured to be divided by the autocorrelation component of the reference light. Still furthermore, in calculating a component of the light, the above division result may be configured to be divided by wavelength dispersion in the optical amplifier used for amplifying the returning light. The wavelength spectrum data obtained from the acquired returning light, the reference light and the combined light may be used to form an image without having depth resolution.

According to the optical tomographic imaging apparatus and the method of imaging an optical tomographic image according to the present embodiment, measurement can be performed while noises caused by the autocorrelation components of the reference light and the returning light are sequentially being removed according to a position of an object to be detected, providing a high-resolution tomographic image.

[Storage Medium and Program]

As another embodiment, the above imaging method according to the present embodiment may be stored in a computer-readable storage medium (for example, a flexible disk, a hard disk, an optical disk, a magneto-optical disk, a CD-ROM, a CD-R, a magnetic tape, a nonvolatile memory card, a ROM, an EEPROM, a blue ray disk and the like) as a program to be executed by a computer. As further another embodiment, there may be a program for causing a computer to execute the above imaging method.

EXAMPLES

Examples of the present invention are described below.

Example 1

Michelson Type Interferometer

Figure 2A:
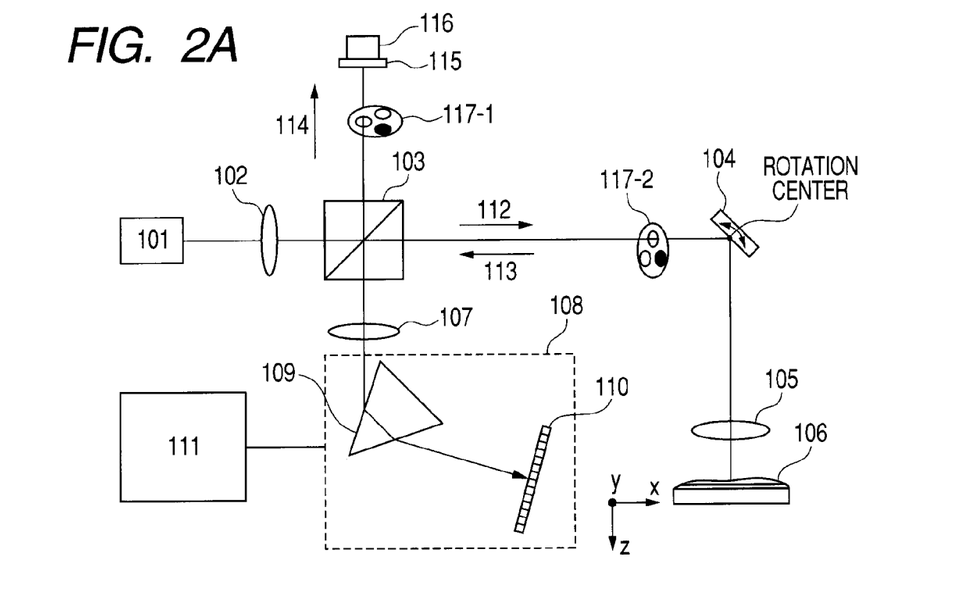
FIGS. 2A and 2B are schematic diagrams for describing optical systems of the imaging apparatus using the optical coherence tomography according to examples 1 and 2.

There is described an example of an imaging apparatus (or an optical tomographic imaging apparatus) using optical coherence tomography according to the example 1 with reference to FIG. 2A. The optical tomographic imaging apparatus of the present example forms a Michelson type interferometer as a whole and uses a mechanical mechanism in a part of controlling light.

Light emitted from a light source 101 passes through a lens 102 and is split into the measuring light 112 and the reference light 114 by a beam splitter 103. The measuring light 112 reaches the object 106 to be detected 106 through the XY scanner 104 and an object lens 105. A light transmissive film is arranged on the object 106 to be detected. The returning light 113 scattered and reflected by the surface and interface of the film returns through the object lens 105, the XY scanner 104 and the beam splitter 103 in this order and reaches a spectroscope 108 through an imaging lens 107. On the other hand, the reference light 114 is reflected by the reference mirror 115. The reference mirror 115 can adjust optical path length with the aid of a position adjusting device 116. The reference light 114 is added to the returning light by the beam splitter 103. The reference light 114 and the returning light 113 can be cut off by rotary shutters 117-1 and 117-2 respectively. The shutters 117-1 and 117-2 can continuously control the transmittance and cutoff of light by the use of a control unit (not shown). Of course the shutter does not need to be of a rotary type. A slide shutter may be movably arranged on the light path.

The light source 101 uses a super luminescent diode (SLD) which is a typical low-coherent light source. The center wavelength thereof is 830 nm, for example, and the band width is 50 nm. The band width is an important factor because it affects the resolution in the optical axis of the tomographic image to be obtained. Although the SLD has been selected as the light source, any others that can emit low-coherent light may be used, e.g. an amplified spontaneous emission (ASE) light source may be used. Of course other light sources such as a halogen lamp and the like may be used depending upon the contents of the object to be detected. However, the wavelength affects the resolution in the lateral direction of the tomographic image to be obtained, so that it is desirable to use a short wavelength in attaching importance to lateral resolution.

The spectroscope 108 includes the prism 109 and the imaging device 110 and disperses the returning light 113, the reference light 114 and the combined light, respectively. The dispersed light is captured by the imaging device in the spectroscope 108 as the spectrum data of wavelength. The spectrum data of wavelength imaged by the imaging device is analyzed by a computer 111. The computer 111 has functions not only to analyze the data, but also to issue instructions for storing data, displaying an image and measuring data. The XY scanner 104 raster-scans the measuring light 112 over the object 106 to be detected in the direction perpendicular to the optical axis with the aid of computer control to obtain the cross section image of the object 106 to be detected.

Figure 3A:
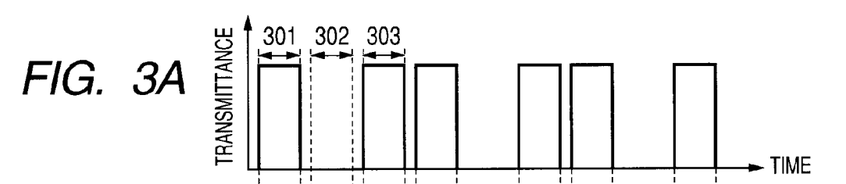
FIGS. 3A, 3B, 3C, 3D and 3E are timing charts for describing control profiles for reference and returning lights in examples 1 to 3.
Figure 3B:
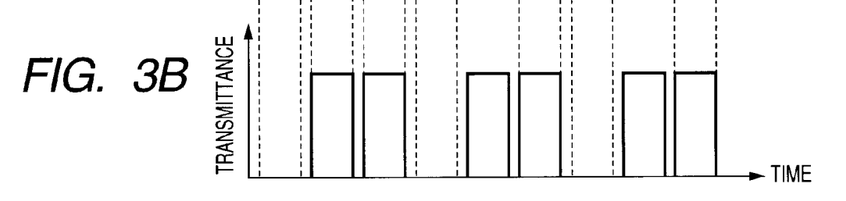

A time profile of transmittance of the reference light 114 and the returning light 113 in the present example is described below with reference to FIGS. 3A and 3B. FIGS. 3A and 3B are timing charts for describing examples of time profiles of transmittance of the reference light 114 and the returning light 113 respectively, where transmittance is 0% or 100% in the examples.

For the rotary shutter, a disk in the same circumference of which three holes are made is used and a blocking member is arranged in one hole. The rotation of the disk at constant speed provides such a profile. The reference light, the returning light and the combined light are obtained by intervals 301, 302 and 303 illustrated in FIG. 3A respectively. Of course, the computer 111 controls the spectroscope 108 and the XY scanner 104 based on the set control profile.

Transmittance does not need to be 100% and may be changed in the case where only the reference light is measured and where the combined light is measured. For the rotary shutter, for example, the use of a ND filter in the hole of the disk enables transmittance to be changed. If the use of the ND filter changes optical path length, a glass member which is the same in optical path length is arranged in the hole of the other disk. The time intervals 301, 302 and 303 do not need to be equal to one another. Since the reference light is large in amount, the time intervals can be short. The use of a slide shutter allows optionally changing the time interval of the shutter. If the wavelength spectrum of the light source is temporally stable, a profile for continuously obtaining the returning light and the combined light can be accepted. In this case, the wavelength spectrum of the light source needs to be previously obtained.

Figure 4:
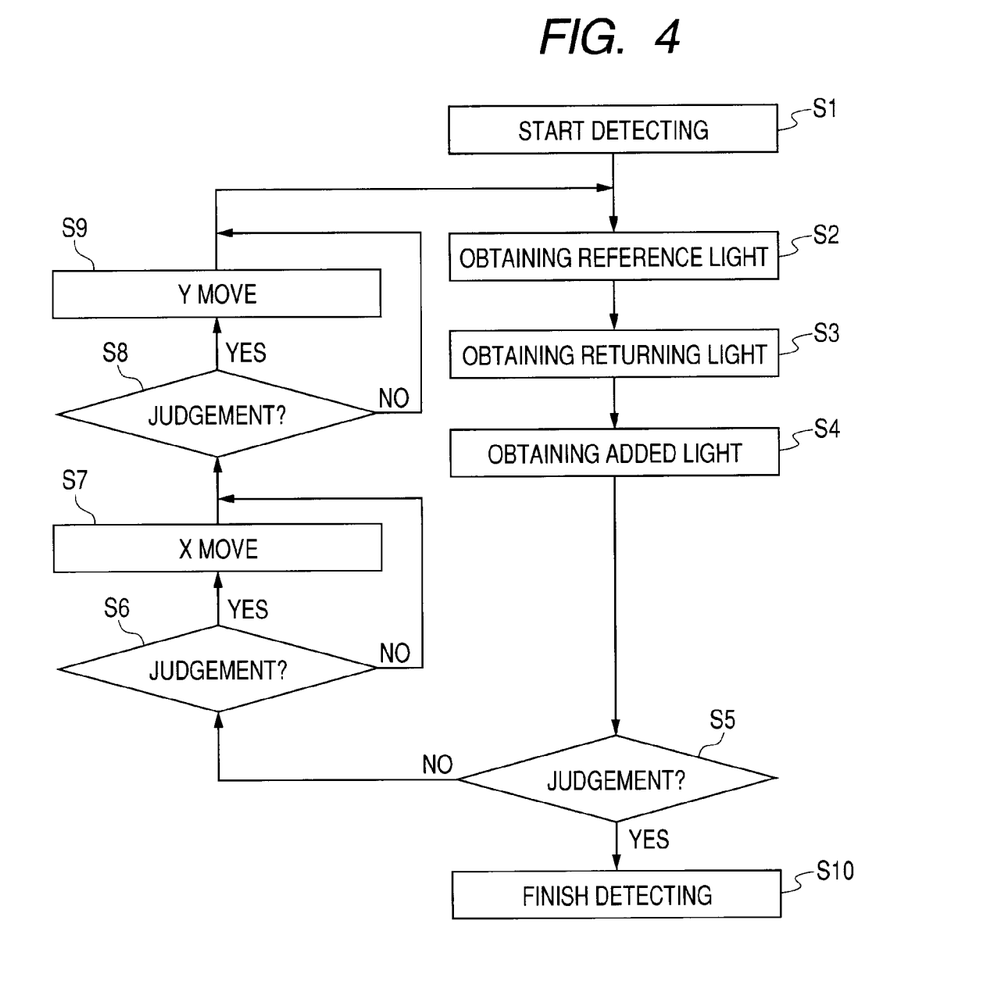
FIG. 4 is a flow chart for measurement in the example 1.

Processing behavior in the present example is described below with reference to FIG. 4. FIG. 4 is a flow chart for describing the processing behavior in the present example.

In step S1, measurement is started.

In step S2, the reference light 114 is obtained by the imaging device 110 while the measuring light 112 is cutoff by the shutter 117-2 and stored in a memory.

Intensity $I_r(k)$ being the autocorrelation component of the reference light 114 is expressed by an equation 1 with a wave number k and the electric field of the reference light as $E_r(k)$.

$$I_r(k) = \{E_r(k)\}^2 \quad \text{(Equation 1)}$$

Of course, a general spectroscope acquires the spectrum of a wavelength λ.

The spectrum of the wavelength λ is converted to the spectrum of a wave number by using the relationship of the wave number k to the wavelength λ being k=2π/λ. It is desirable to resample a spectrum equally spaced in the wave number in consideration of Fourier transformation in the later process.

Herein, the spectrum is considered to be equally spaced in the wave number. If the spectrum of the reference light is not temporally changed, the reference light 114 may be previously obtained and stored in the memory.

In step S3, the returning light 113 is obtained by the imaging device 110 while the reference light 114 is cutoff by the shutter 117-1.

There is determined the relationship among the intensity $I_s(k)$ of the returning light 113, the electric field $E_s(k)$ of the returning light 113 and the electric field $E_r(k)$ of the reference light 114.

Figure 5:
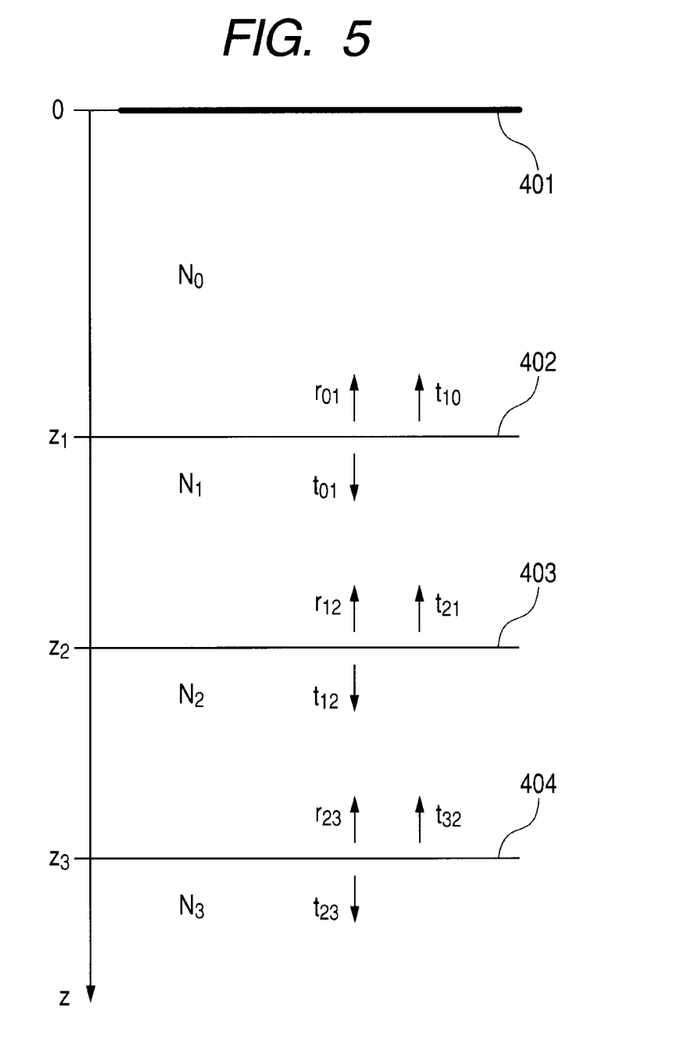
FIG. 5 is a schematic diagram for describing the structure of tomogram and a relationship of reflectivity and transmittance in the example 1.

As illustrated in FIG. 5, the spatial distance of i-th interface away from a position 401 of an equivalent reference mirror 401 is taken as $z_i$, a reflectivity of the interface is taken as $R(z_i)$ and a round-trip transmittance between the reference mirror and the position $z_i$ is taken as $T(z_i)$.

The use of an average refractive index to the position $z_i$ taken as $n(z_i)$ allows representing an intensity $I_s(k)$ being the autocorrelation component of the returning light 113 by an equation 2.

Incidentally, herein, it is assumed that the reference light 114 and the measuring light 112 are equally split and the spectra thereof are equal to each other. An imaginary unit is denoted by "j".

$$I_s(k) = \{E_s(k)\}^2 = \left\{\sum_{z_i} T(z_i)R(z_i)e^{-j2kn(z_i)z_i}E_r(k)\right\}^2 \quad \text{(Equation 2)}$$

Thus, the spectrum of the returning light 113 has information in the depth direction.

The depth information varies with the XY coordinate of the object to be detected and measured, so that it is required for obtaining two or three dimensional image.

Incidentally, the integration of the equation 2 with respect to a desired wave number provides the intensity signal of the entire returning light 113 without depth resolution.

This can be used as a confocal laser scanning ophthalmoscopy image. The equation 2 may be imaged only by a specific wave number without integration.

There is described below the reflectivity $R(z_i)$ and the round-trip transmittance $T(z_i)$ between the reference mirror located in an optically equivalent position and the position $z_i$.

A reflectivity and a transmittance at an interface in the case where light is incident on a substance with a refractive index $n_t$ from a substance with a refractive index $n_s$ can be represented by equations 3 and 4 respectively.

When the refractive index is not changed, the reflectivity is 0 and the transmittance is 1.

The phase is reversed at a negative reflectivity.

For the sake of simplicity, there is neglected the influence of absorption and multiple reflection in a medium.

$$r(z_{st}) = \frac{n_s - n_t}{n_s + n_t} \quad \text{(Equation 3)}$$

$$t(z_{st}) = \frac{2n_s}{n_s + n_t} \quad \text{(Equation 4)}$$

The examples of the reflectivity $R(z_i)$ and the round-trip transmittance $T(z_i)$ are illustrated by using tomogram with structure as illustrated in FIG. 5.

The tomogram in this case is formed of a first interface 402, a second interface 403 and a third interface 404. In addition, the reference mirror 401 is illustrated in an optically equivalent position.

The refractive index of the reference mirror located in an optically equivalent position and the first interface is taken as $N_o$, and the reflectivity and the transmittance of light incident on the first interface from the side of the reference mirror are taken as $r_{01}$ and $t_{01}$ respectively.

On the other hand, the transmittance of light incident on the first interface from the side of the second interface is taken as $t_{10}$.

Similarly, as illustrated in FIG. 5, the refractive index of the first interface and the second interface is taken as $N_1$, the reflectivity and the transmittance of light incident on the second interface from the side of first interface are taken as $r_{12}$ and $t_{12}$ respectively and the transmittance of light incident on the second interface from the side of the third interface is taken as $t_{21}$.

The refractive index of the second interface and the third interface is taken as $N_2$, the reflectivity and the transmittance of light incident on the third interface from the side of the second interface are taken as $r_{23}$ and $t_{23}$ respectively and, on the other hand, the transmittance of light incident on the third interface from the side of the fourth interface is taken as $t_{32}$. The refractive index of the third interface and the fourth interface is taken as $N_3$.

With the use of the above symbols, for example, the reflectivity of light incident on the third interface from the side of the reference mirror can be expressed by an equation 5.

$$R(z_3) = r_{23} = \frac{n_2 - n_3}{n_2 + n_3} \quad \text{(Equation 5)}$$

On the other hand, the round-trip transmittance can be obtained by multiplying together the transmittances of the interfaces through which light passes and represented by an equation 6.

$$T(z_3) = t_{01}t_{12}t_{21}t_{10} = \frac{2n_0}{n_0+n_1}\frac{2n_1}{n_1+n_2}\frac{2n_2}{n_2+n_1}\frac{2n_1}{n_1+n_0} \quad \text{(Equation 6)}$$

In step S4, the combined light $L_{add}(k)$ of the reference light 114 and the returning light 113 is obtained by the imaging device 110 while the shutter 117-1 and the shutter 117-2 does not cutoff the light. At this point, a coherence component $I_{rs}(k)$ as well as the autocorrelation components of the reference light 114 and the returning light 113 appears. The combined light $I_{add}(k)$ can be represented by an equation 7.

$$I_{add}(k) = I_r(k) + I_{rs}(k) + I_s(k) = \{E_r(k) + E_s(k)\}^2 \quad \text{(Equation 7)}$$

The subtraction of the equations 1 and 2 from the equation 7 provides the coherence component $I_{rs}(k)$. This can be expressed by the following equation 8.

$$I_{rs}(k) = E_r(k)E_s^*(k) + E_r^*(k)E_s(k) = \sum_{z_i} 2R(z_i)T(z_i)\cos\{2kn(z_i)z_i\}E_r^2(k) \quad \text{(Equation 8)}$$

The division of the subtraction result of the equation 8 by the autocorrelation component of the reference light 114 (equation 1) provides a standardized spectrum $S_{rs}(k)$ represented by the following equation 9. This corresponds to the elimination of influence of wavelength dispersion of the light source 101 and the spectroscope 108.

$$S_{rs}(k) = \sum_{z_i} 2R(z_i)T(z_i)\cos\{2kn(z_i)z_i\} \quad \text{(Equation 9)}$$

The Fourier transformation of the equation 9 causes a signal corresponding to $R(z_i)T(z_i)$ to appear in a position of an optical distance $n(z_i)z_i$, providing a tomographic image. The equations 8 and 9 may be calculated after each of the desired returning light 113, reference light 114 and combined light have been obtained.

The results of Fourier transformation in the equation 9 are accumulated to be used as a confocal laser scanning ophthalmoscopy image. That is to say, actually, light returning from the object 106 is weak, so that the returning light 113 expressed by the equation 2 sometimes cannot be measured. In such case, the multiplication of the reference light 114 by the returning light as expressed by the equation 7 allows the detection of the component of the returning light 113.

In step S5, a judgment is made as to whether a desired region has been measured. If the measurement is finished, the process proceeds to step S10.

If the measurement is not finished, the process proceeds to step S6. The term "desired region" refers to, for example, 512 points at a 20-μm step in the X direction or 512 points at a 20-μm step in the Y direction on the object to be detected. Of course, the distance and the number of points may be different with an object to be detected and an apparatus.

In step S6, a judgment is made as to whether movement is performed in the X direction.

If the movement is performed in the X direction, the process proceeds to step S7. If not, the process proceeds to step S8.

In step S7, the movement is performed by a desired distance in the X direction and the process proceeds to step S8. The term "desired distance" is 20 μl, for example.

In step S8, a judgment is made as to whether movement is performed in the Y direction.

If the movement is performed in the Y direction, the process proceeds to step S9. If not, the process proceeds to step S2.

In step S9, the movement is performed by a desired distance in the Y direction and the process proceeds to step S2. The term "desired distance" is 20 μm, for example.

Finally, in step S10, measurement is finished.

Of course, as being an ideal measurement result, the interface in FIG. 5 is displayed as a tomographic image.

There is described below the effect of removing the autocorrelation components.

The combined light is expressed by the equation 7 and the required components are expressed by the equation 8. The autocorrelation components of the reference light 114 and the returning light 113 are noises, so that the components need to be removed.

In the case where an SLD is used as a general light source, the autocorrelation component of the reference light, as an image which gradually attenuates from a peak as its original point to a position away from the original point, overlaps with the tomographic image. In addition, the autocorrelation component is folded, as shown in the equation 8, distorting the tomographic image.

On the other hand, in the example of FIG. 5 to be described below, the autocorrelation components of the returning light 113 interfere with each other at the first, second and third interfaces.

Those autocorrelation components overlap the tomographic image to produce noises. In other words, an image appears in a position of $N_1(z_2-z_1)$, $N_2(z_3-z_2)$, $N_1(z_2-z_1)+N_2(z_3-z_2)$ on the image formed at $n(z_i)z_i$.

In general, the autocorrelation component of the returning light is more extensive than the component attributed to the reference light.

When the autocorrelation component of the returning light is not removed, the distance between the reference mirror located in an optically equivalent position and the first mirror needs to be greater than the thickness of layer of the object to be detected. Thereby, the tomographic component can be separated from the autocorrelation component even if a layer is displayed as if to lie between the reference mirror 401 located in an optically equivalent position and the first mirror 402.

The removal of the autocorrelation components of the reference light 114 and the returning light 113 allows the reference mirror 401 located in an optically equivalent position to be arranged in a position near the first interface.

In general, the arrangement of the reference mirror 401 located in an optically equivalent position in a position near the first interface enables a high sensitivity measurement, which is especially effective for the object to be detected that is low in reflectivity like the eyes.

The division with the spectrum of the reference light 114 eliminates the distortion of a tomographic image to provide a high resolution image.

There is conceived a method of measuring the autocorrelation components of the reference light 114 and the returning light 113 using a plurality of spectroscopes. According to the present example, the method using a single spectroscope is realized, resulting in enabling with a low cost. There is no need for considering the individual difference between spectroscopes.

Example 2

Mach-Zehnder Type Interferometer

Figure 2B:
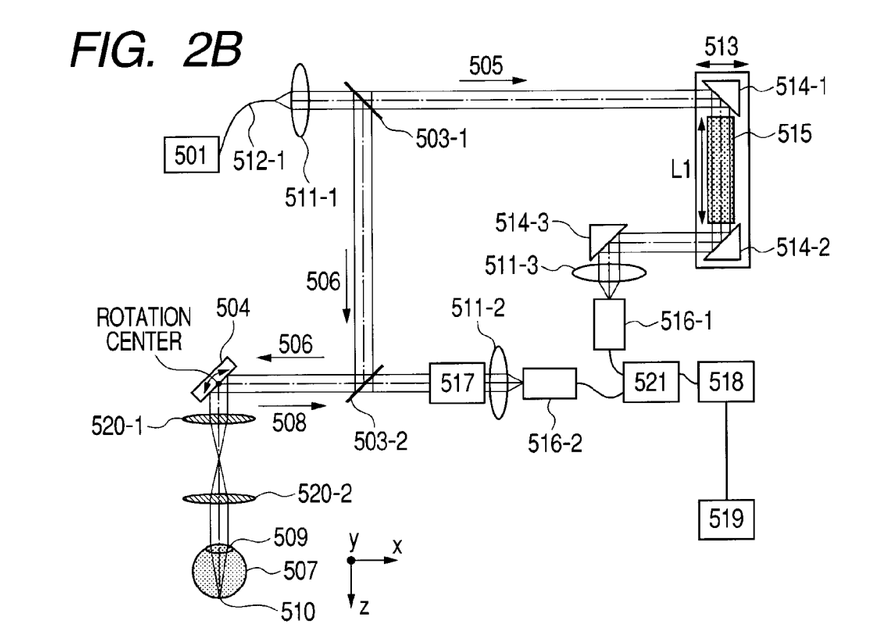

There is described an example of an optical tomographic imaging apparatus according to the example 2 with reference to FIG. 2B. FIG. 2B is a schematic diagram for describing an optical system for the optical tomographic imaging apparatus in the present example. The optical tomographic imaging apparatus of the present example forms a Mach-Zehnder type interferometer as a whole and uses an electrical mechanism in a part of controlling light.

In the present example, the object to be detected is the eyes, so that the returning light is small in amount. For this reason, the use of the optical amplifier 517 for amplifying the returning light enables a high-speed light control.

Light emitted from a light source 501 is conducted to a lens 511-1 to 511-3 through a single mode fiber 512-1 and split into the reference light 505 and the measuring light 506 by a beam splitter 503-1 and 503-2. The measuring light 506 is reflected or scattered by the eye as an object to be detected 507 being the object to be detected and returned as returning light 508. The reference light and the returning light are incident on a spectroscope 518 through a fiber coupler 521. Data such as wavelength spectrum obtained by the spectroscope is captured in a computer 519. The light source 501 uses a super luminescent diode (SLD) being a typical low-coherent light source. In consideration of measuring the eyes, near infrared light is suitable as a wavelength.

The light path for the reference light 505 is described below.

The reference light 505 split by the beam splitter 503-1 is sequentially incident on mirrors 514-1, 514-2 and 514-3 to be changed in its direction, converged by a lens 511-3 and incident on an optical switch 516-1. There is used a directivity-coupler optical switch in which light is switched by changing a refractive index as the optical switch. Of course, there may be used a Mach-Zehnder type interferometer optical switch, a gate-type optical switch using an optical gate element capable of controlling the transmittance of light and a total internal reflection type optical switch using a semiconductor.

A dispersion compensation glass 515 is L1 in length, which desirably doubles the depth of a normal eye. The dispersion compensation glass 515 compensates dispersion of the measuring light 506 traveling to and from the eye 507 for the reference light 505.

The length L is taken as 46 mm, which doubles the diameter of an average Japanese eyeball of 23 mm. An electric stage 513 can be moved in the direction indicated by an arrow in the figure and adjust and control the light path length of the reference light 505.

The light path for the measuring light 506 is described below.

The measuring light 506 split by the beam splitter 503-1 is reflected by the beam splitter 503-2 and then incident on the mirror of an XY scanner 504.

The XY scanner 504 performs a raster-scan on a retina 510 in the direction perpendicular to the optical axis.

The center of the measuring light 506 is adjusted to coincide with the rotation center of the mirror of the XY scanner 504.

The lenses 520-1 and 520-2 is an optical system for scanning the retina 510 and plays a role to scan the measuring light 506 over the retina 510 with the vicinity of the cornea 509 as fulcrum.

The lenses 520-1 and 520-2 are 50 mm and 50 mm in focal distance respectively. The incidence of the measuring light 506 on the eye 507 produces the returning light 508 by reflection and/or scatter from the retina 510.

The returning light 508 passes through the optical amplifier 517, is converged by a lens 511-2 and led to the spectroscope 518 through an optical switch 516-2 and the fiber coupler 521.

The optical amplifier uses a semiconductor amplifier. Some optical amplifiers can be used as a gate element for changing transmittance.

The use of this as the gate-type optical switch allows the elimination of the optical amplifier 517 and the integration of the optical switch 516 and the fiber coupler 521.

Figure 3C:
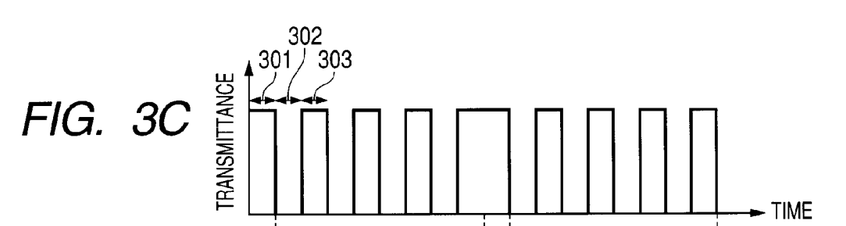
Figure 3D:
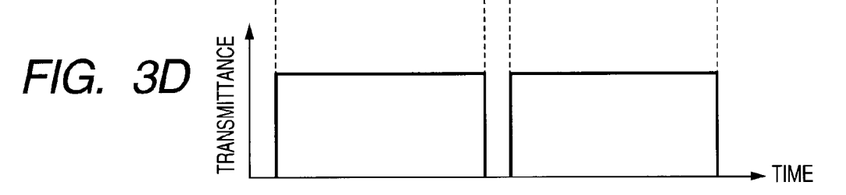

A time profile of transmittance of the reference light and the returning light in the present example is described below with reference to FIGS. 3C and 3D. FIGS. 3C and 3D are profiles of the reference light and the returning light respectively. Transmittance is desirably 0% or 100% but a waveguide light path sometimes generates a little loss and leakage. The reference light, the returning light and the combined light are obtained by intervals 301, 302 and 303 illustrated in FIG. 3C respectively.

Figure 6:
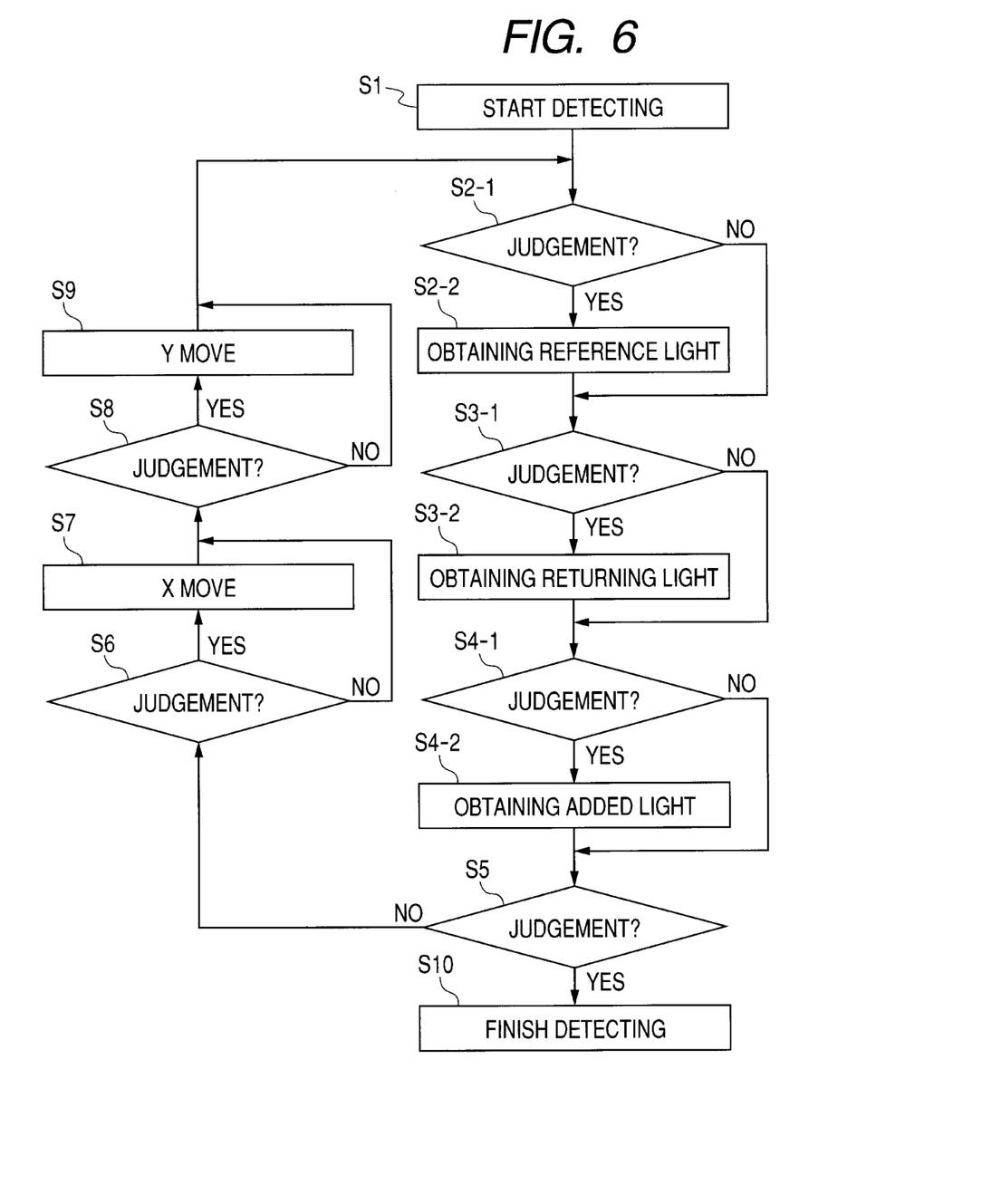
FIG. 6 is a flow chart of measurement in the example 2.

Signal processing in the present example is described below with reference to FIG. 6. FIG. 6 is a flow chart for describing the signal processing in the present example.

In step S1, measurement is started.

In step S2-1, a judgment is made as to whether the reference light is obtained.

The judgment as to whether the reference light is obtained is made based on a control profile.

If the reference light is obtained, the process proceeds to step S2-2, and if no, the process proceeds to step S3-1.

In step S2-2, the reference light 505 is obtained by a spectroscope 518 while the returning light 508 is cutoff by the optical switch 516-2 and stored in a memory. Intensity $I_r(k)$ being the autocorrelation component of the reference light is expressed by the equation 1.

In step S3-1, a judgment is made as to whether the returning light is obtained.

The judgment as to whether the returning light is obtained is made based on the control profile.

If the returning light is obtained, the process proceeds to step S3-2, and if no, the process proceeds to step S4-1.

In step S3-2, the returning light 508 is obtained by a spectroscope 518 while the reference light 505 is cutoff by the optical switch 516-1.

The intensity $I_s(k)$ being the autocorrelation component of the returning light is different from that of the example 1 and can be expressed by an equation 10 in which the equation 2 is multiplied by a wavelength dispersion G(k) of the optical amplifier.

$$I_s(k) = \{E_s(k)\}^2 = \left\{\sum_{z_i} R(z_i)T(z_i)e^{-j2kn(z_i)z_i}G(k)E_r(k)\right\}^2 \quad \text{(Equation 10)}$$

If wavelength dispersion generated due to a difference between devices in the light path is included in G(k), a range may be increased.

In step S4-1, a judgment is made as to whether the combined light is obtained. The judgment as to whether the combined light is obtained is made based on the control profile.

If the combined light is obtained, the process proceeds to step S4-2, and if no, the process proceeds to step S5.

In step S4-2, the combined light $I_{add}(k)$ is obtained by a spectroscope 518 while the reference light 505 and the returning light 508 is cutoff by the optical switch 516-1 and 516-2, respectively. At this point, a coherence component $I_{rs}(k)$ as well as the autocorrelation components of the reference light and the returning light appears. The subtraction of the equations 1 and 10 from the combined light $I_{add}(k)$ provides an equation 11.

$$I_{rs}(k) = I_{rs}(k) = E_r(k)E_s^*(k) + E_r^*(k)E_s(k) = \sum_{z_i} 2R(z_i)T(z_i)\cos\{2kn(z_i)z_i\}G(k)E_r^2(k) \quad \text{(Equation 11)}$$

The division of the equation 11 by the autocorrelation component of the reference light (equation 1) provides a standardized spectrum $S_{rs}(k)$ represented by an equation 12.

$$S_{rs}(k) = \sum_{z_i} 2R(z_i)T(z_i)\cos\{2kn(z_i)z_i\}G(k) \quad \text{(Equation 12)}$$

Since the equation 12 is different from the equation 9 in that the equation 12 is multiplied by the wavelength dispersion G(k) of the optical amplifier, the division of the equation 12 by G(k) provides the equation 9 in the example 1. Incidentally, the wavelength dispersion of the optical amplifier is previously obtained and stored in a memory.

Specifically, a mirror, for example, is arranged instead of the eyes, the spectra of the reference light and the returning light are obtained and calculated to obtain the wavelength dispersion of the optical amplifier.

In step S5, a judgment is made as to whether measurement is finished.

If the measurement is to be finished, the process proceeds to step S10. If no, the process proceeds to step S6.

In step S6, a judgment is made as to whether movement is performed in the X direction.

If the movement is performed in the X direction, the process proceeds to step S7. If not, the process proceeds to step S8.

In step S7, the movement is performed by a desired distance in the X direction and the process proceeds to step S8.

In step S8, a judgment is made as to whether movement is performed in the Y direction.

If the movement is performed in the Y direction, the process proceeds to step S9. If not, the process proceeds to step S2-1.

In step S9, the movement is performed by a desired distance in the Y direction and the process proceeds to step S2-1.

If it is finally determined in step S5 through the above steps that measurement is finished, the process proceeds to step S10 to finish the measurement.

In the present example, the use of an electrical optical switch allows a high speed measurement. Furthermore, the use of the optical amplifier enables even weak light to be measured. Still furthermore, the calculation provides a high resolution tomographic image at a high speed.

Example 3

Shutter

Figure 7:
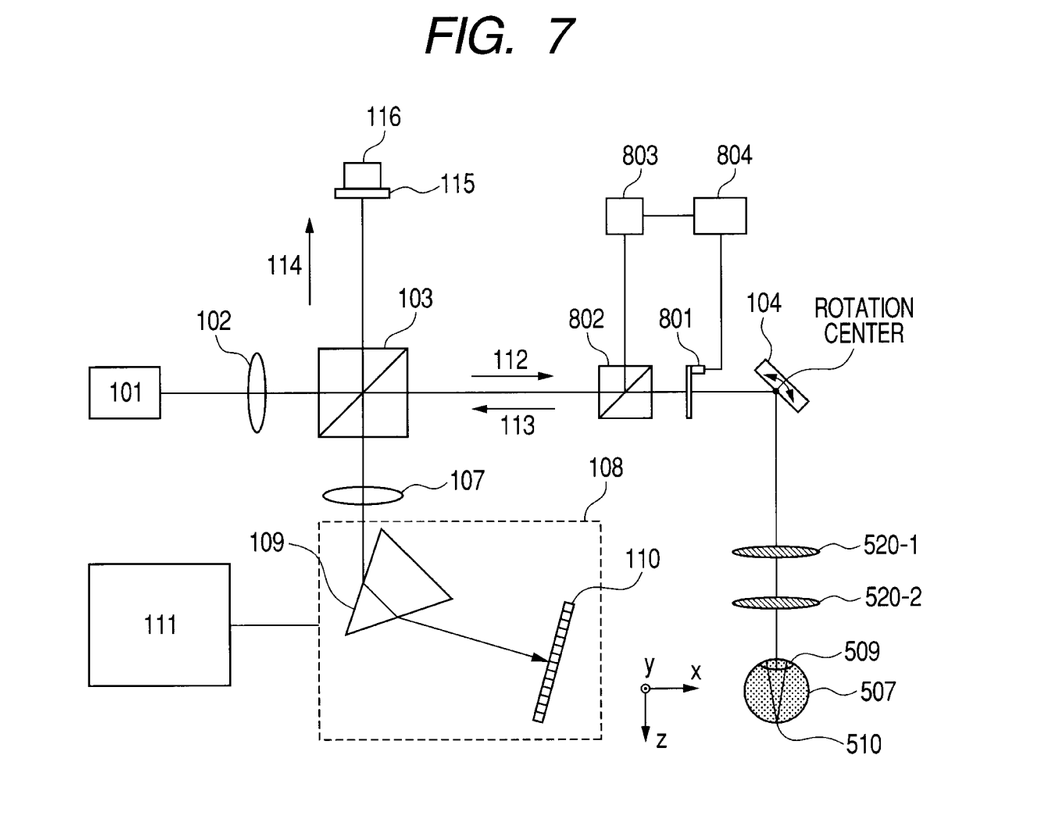
FIG. 7 is a schematic diagram for describing an optical system for an image apparatus using optical coherence tomography in the example 3.

In the example 3, there is described an example of an ophthalmic OCT apparatus using a safety shutter with reference to FIG. 7. FIG. 7 is a schematic diagram for describing an optical system for the optical tomographic imaging apparatus in the present example. The same reference number refers the same component as in FIGS. 2A and 2B, and the points different from the examples 1 and 2 are described below.

The shutter prevents the measuring light to radiate out of the imaging apparatus when the light quantity of the measuring light is different from the predetermined light quantity (or is out of the range of the predetermined light quantity). A case when the light quantity of the measuring is different from the predetermined light quantity naturally includes a case that the light quantity of the measuring light is smaller or greater than the predetermined light value.

A shutter 801 opens and closes the light path through an electrical circuit in response to instructions from the computer 111. A beam splitter 802 splits the measuring light 112 into a light for a detector 803 and a measuring light for an object to be measured. A detector 803 detects the quantity of light and inputs a signal thereof to an electrical circuit 804. The detector is a photo diode, for example, and a current-voltage converter therein converts current to voltage and the voltage signal is input to the electrical circuit.

The shutter includes electrical-optical, magneto-optic and mechanical shutters. The electrical-optical shutter is formed such that a prism electrode is arranged on an optical deflection element of PLZT:(Pb, La)(Zr, Ti)O$_3$. The application of voltage to the prism electrode changes the refractive index in a prism shape to allow the beam to be bent. Transmittance and cutoff can be switched by the angle of the beam. The response speed ranges from several nanoseconds to several hundred nanoseconds. The magneto-optic shutter is formed such that a magneto-optic element wrapped with a magnetic coil, for example, is arranged between polarizers rectangular to each other. Current flowing into the magnetic coil rotates the polarization plane of the magneto-optic element to control the transmittance and cutoff of light. The response speed ranges from several microseconds to several hundred microseconds. The mechanical shutter changes the angle of the mirror using a MEMS device, for example, enabling switching the transmittance and cutoff of light. The response speed ranges from several hundred microseconds to several milliseconds. Moving a blocking object to and from the light path by means of a magnetic coil allows switching the transmittance and cutoff of light. The response speed ranges from several tens of milliseconds to several hundred milliseconds.

Figure 8:
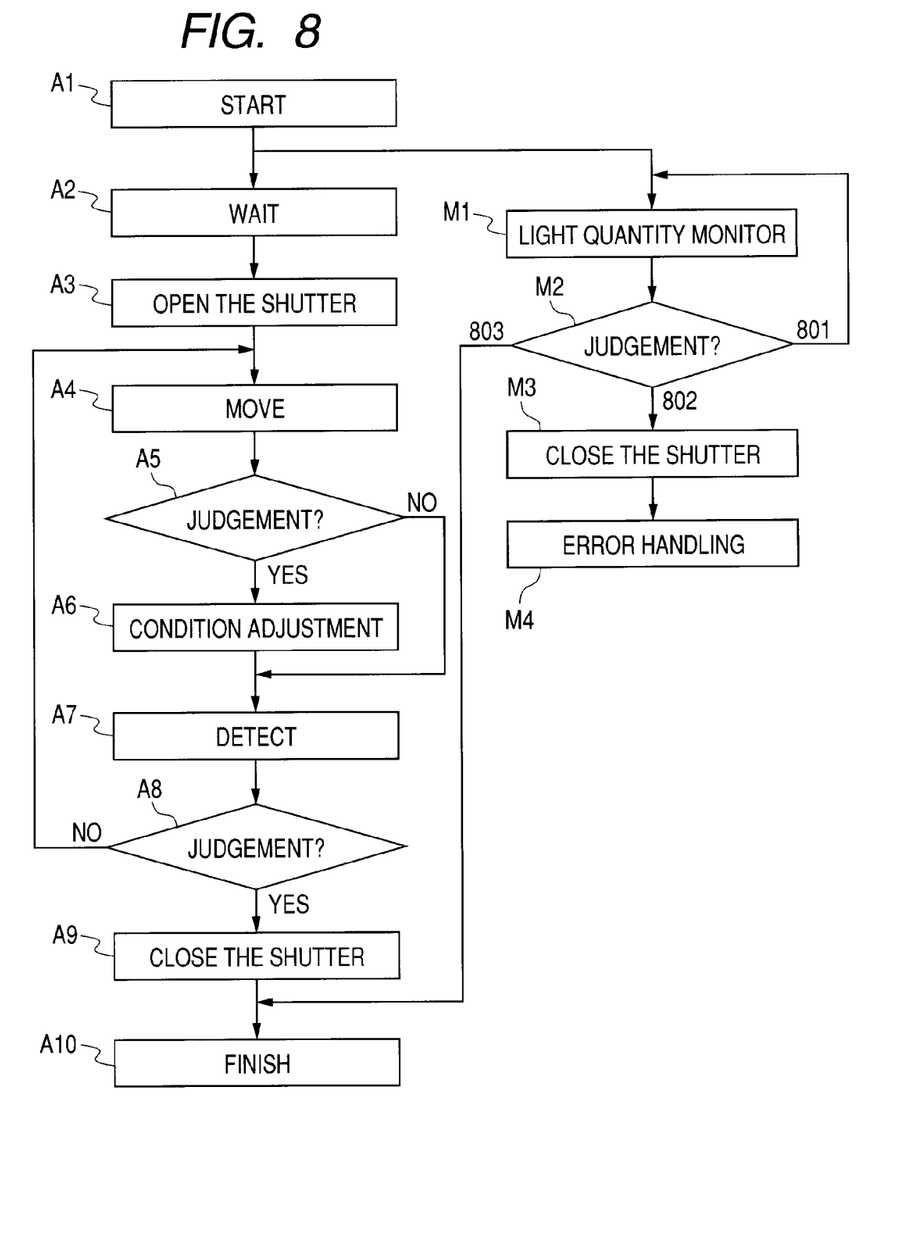
FIG. 8 is a flow chart of measurement in the example 3.

A flow chart of the example 3 is described below with reference to FIG. 8.

The process starts in step A1 and proceeds to steps A2 and M1.

In step M1, the quantity of light is detected by the detector 803 and monitored by the electric circuit 804. The step A2 is a stand-by time until the monitor of quantity of light is surely started and the stand-by time is several tens of milliseconds, for example.

In step M2, a confirmation is made as to whether the quantity of light is within a specified range and measurement is not finished. If the above conditions are satisfied, the process returns to step M1 (801). Note that the specified quantity of light is determined by the standard such as ANSI, e.g., 700 µW. If the quantity of light is not within a specified range, e.g., not within 680-700 µm, the process proceeds to step M3 (802). If measurement is finished, the process proceeds to step A10 and ends (803).

In step M3, if the shutter is opened at this moment, the shutter is closed. Thereafter, the process proceeds to step M4 to process error handling. The processing of error handling means that the acquisition of data by a spectroscope is stopped by a computer to return a scanner and a reference mirror to an initial position, and so on. In addition, an error message is output on a screen of the computer.

In step A3, the shutter is opened. Opening the shutter causes the measuring light to reach the eye to be examined to cause the returning light to reach the spectroscope, enabling the combined light to be measured. The quantity of light is monitored once or more in step M1 during the stand-by time in step A2.

In step A4, the scanner is moved to a desired position. The movement of the scanner refers to scan in the X and Y directions. The scanner is moved in the X and Y directions on the assumption that 3D measurement is performed to obtain data of 512 points×512 points in the XY plane. The X direction is taken as Fast-Axis in which a round-trip scanning is performed at a high speed. The Y direction is taken as Slow-Axis in which a unidirectional scanning is performed at a low speed.

In step A5, a judgment is made as to whether the state of the shutter is changed. The change of state of the shutter changes the state of transmittance or cutoff of light. If the change of state is required, the process proceeds to step A6 to change state of the shutter. If the change of state is not required, the process proceeds to step A7.

In step A7, measurement is performed by a spectroscope 108. When the shutter is closed, the reference light can be measured because the returning light does not exist. The intensity of the reference light corresponds to the equation 1. On the other hand, when the shutter is opened, the combined light can be measured because the returning light exists. The intensity of the combined light corresponds to the equation 7. In general, the autocorrelation component of the returning light from the eye to be examined is very weak and the intensity of the returning light (equation 2) can be regarded as zero. For this reason, the reference light is subtracted from the combined light and the result is divided by the autocorrelation component of the reference light provides the equation 9. The Fourier transformation of the equation 9 provides a tomographic image. Of course, the above signal processing may be collectively performed after the measurement has been finished.

Figure 3E:
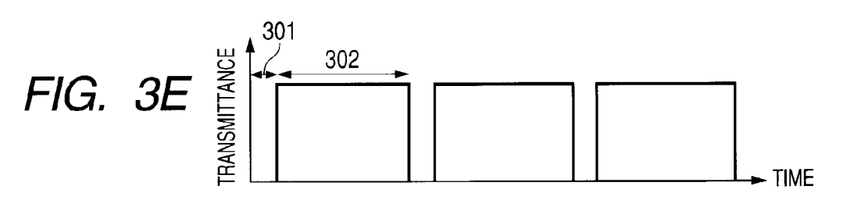

In step A8, a judgment is made as to whether the desired region has been measured. FIG. 3E illustrates the profile of the measuring light controlled by the shutter. The figure illustrates the profile obtained by repeating the steps A4 to A8 three times. The reference light is measured in the interval 301. The stage is moved in the Y direction during the interval 301, and moved back in the X direction by a distance moved during the interval 302. The reference light is measured once during the interval. The combined light is measured in the interval 302. The stage is moved in the X direction at a constant speed during the interval 302 and not moved in the Y direction. The combined light is measured 512 times during the interval.

In step A9, the shutter is closed. When the shutter is originally closed, the shutter is kept as it is.

In step A10, the measurement is finished.

As seen above, in this example, a shutter to shut off the measuring light is located on the measuring light path and the shutter is used while reference light is detected, thereby the stability of the measuring light during the detection is enabled with a very simple circuit configuration.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims priorities from Japanese Patent Applications No. 2008-177158, filed Jul. 7, 2008 and No. 2009-151483, filed Jun. 25, 2009, which are hereby incorporated by reference herein.

The invention claimed is:

1. An imaging apparatus for imaging an object using Fourier-domain optical coherence tomography, the imaging apparatus comprising:

a detecting unit for detecting combined light comprising a returning light from the object and a reference light;

a first switching unit for switching between a first state in which the detecting unit can detect the combined light and a second state in which the detecting unit can detect the reference light;

a second switching unit for switching between the first state and a third state in which the detecting unit can detect the returning light;

a controlling unit for controlling the first switching unit and the second switching unit such that the detection of the combined light in the first state, the detection of the reference light in the second state, and the detection of the returning light in the third state are continuously and repeatedly changed, while it takes not less time for the detection of the returning light in the third state than the detection of the reference light in the second state; and an interferometric information acquiring unit for acquiring interferometric information on the returning light and the reference light by using the combined light detected by the detecting unit in the first state, the reference light detected by the detecting unit in the second state, and the returning light detected by the detecting unit in the third state.

2. The imaging apparatus according to claim 1, wherein the first switching unit is configured such that one of a light path of the measuring light to be irradiated on the object and a light path of the returning light can be blocked, or the second switching unit is configured such that the light path of the reference light can be blocked, and wherein the second state and the third state is in the blocked state.

3. The imaging apparatus according to claim 1, wherein the first switching unit is configured such that the transmittance of one of the measuring light to be irradiated on the object and the returning light can be controlled, or the second switching unit is configured such that the transmittance of the reference light can be controlled.

4. The imaging apparatus according to claim 1, further comprising:

a light quantity detecting unit for detecting the quantity of the measuring light to be irradiated on the object; and a comparing unit for comparing the detected light quantity with a predetermined value, wherein when the measuring light quantity is different from the predetermined value, the first switching unit switches to the second state by blocking the measuring light.

5. The imaging apparatus according to claim 1, wherein the first switching unit is configured such that one of the light path of the measuring light to be irradiated on the object and the light path of the returning light can be changed, or the second switching unit is configured such that the light path of the reference light can be changed, and wherein the second state or the third state is the changed state.

6. The imaging apparatus according to claim 1, wherein the controlling unit controls one of the first switching unit and the second switching unit based on a predetermined timing, and the combined light is detected by the detecting unit at the timing of the first state.

7. The imaging apparatus according to claim 1, further comprising:

a light source for emitting light;

a splitting unit for splitting light from the light source into the reference light and the measuring light to be irradiated on the object;

a subtracting unit for subtracting the autocorrelation components of the reference light and the autocorrelation component of the returning light from the combined light detected by the detecting unit;

a standardizing unit for standardizing the subtraction result by the autocorrelation component of the reference light;

a transforming unit for Fourier-transforming the standardization result; and a tomographic image acquiring unit for obtaining a tomographic image of the object to be detected.

8. An imaging method for imaging an object using a Fourier domain optical coherence tomography, the imaging method comprising:

switching between (a) a first state in which the combined light comprising a returning light from the object and a reference light can be detected and (b) a second state in which the reference light can be detected;

switching between the first state and (c) a third state in which the returning light can be detected; and obtaining interferometric information on the returning light and the reference light by using the combined light detected in the first state, the reference light detected in the second state, and the returning light detected in the third state, wherein the detection of the combined light in the first state, the detection of the reference light in the second state, and the detection of the returning light in the third state are continuously and repeatedly changed, while it takes not less time for the detection of the returning light in the third state than the detection of the reference light in the second state.

9. The imaging method according to claim 8, further comprising:

subtracting the autocorrelation component of the reference light and the autocorrelation component of the returning light from the combined light;

standardizing the subtracted value by the autocorrelation component of the reference light;

Fourier-transforming the standardized result; and obtaining a tomographic image of the object to be detected.

10. The imaging method according to claim 8, further comprising:

detecting the light quantity of the measuring light to be irradiated on the object; and changing to the second state by blocking the measuring light when the light quantity is different from a predetermined light quantity.

11. A non-transitory computer-readable storage medium storing a program for causing a computer to execute the imaging method according to claim 8.

12. A non-transitory program causing a computer to execute the imaging method according to claim 8.

13. The imaging apparatus according to claim 1, further comprising:

a tomography image acquiring unit which acquires, from the information of the tomography image of the object based on the intensity of the combined light, a tomography image in which the information based on the intensity of the reference light is reduced.

14. The imaging apparatus according to claim 13, further comprising:

a subtracting unit which subtracts the information which is based on the intensity of the autocorrelation component of the reference light, from the information of the tomography image of the object which is based on the intensity of the combined light, wherein the tomography image acquiring unit acquires the reduced tomography image based on the subtracting result of the subtracting unit.

* * * * *